United States Patent
Mehl

(10) Patent No.: US 10,450,440 B2
(45) Date of Patent: Oct. 22, 2019

(54) CLARIFYING AGENT COMPOSITION AND POLYOLEFIN COMPOSITION COMPRISING THE SAME

(71) Applicant: Milliken & Company, Spartanburg, SC (US)

(72) Inventor: Nathan A. Mehl, Spartanburg, SC (US)

(73) Assignee: Milliken & Company, Spartanburg, SC (US)

(*) Notice: Subject to any disclaimer, the term of this patent is extended or adjusted under 35 U.S.C. 154(b) by 0 days.

(21) Appl. No.: 15/382,169

(22) Filed: Dec. 16, 2016

(65) Prior Publication Data

US 2017/0190872 A1  Jul. 6, 2017

Related U.S. Application Data

(60) Provisional application No. 62/274,096, filed on Dec. 31, 2015.

(51) Int. Cl.
*C08K 5/1575* (2006.01)
*C07D 319/06* (2006.01)

(52) U.S. Cl.
CPC .......... *C08K 5/1575* (2013.01); *C07D 319/06* (2013.01); *C08K 2201/014* (2013.01)

(58) Field of Classification Search
CPC ............................ C08K 5/1575; C07D 319/06
USPC ........................................................ 524/107
See application file for complete search history.

(56) References Cited

U.S. PATENT DOCUMENTS

| | | | |
|---|---|---|---|
| 4,371,645 A | 2/1983 | Mahaffey, Jr. | |
| 4,611,024 A | 9/1986 | Wolfe | |
| 5,049,605 A | 9/1991 | Rekers | |
| 5,731,474 A | 3/1998 | Scrivens et al. | |
| 6,582,503 B2 | 1/2003 | Dotson et al. | |
| 7,157,510 B2 | 1/2007 | Xie et al. | |
| 7,262,236 B2 | 8/2007 | Xie et al. | |
| 8,022,133 B2 | 9/2011 | Xu et al. | |
| 2002/0188044 A1* | 12/2002 | Dotson | C08K 5/1575 524/108 |
| 2003/0008953 A1 | 1/2003 | Dotson et al. | |
| 2006/0079720 A1* | 4/2006 | Xie | C07D 493/04 568/592 |
| 2006/0173108 A1 | 8/2006 | Xu et al. | |
| 2013/0289176 A1 | 10/2013 | Li et al. | |
| 2013/0296580 A1 | 11/2013 | Uppara et al. | |

FOREIGN PATENT DOCUMENTS

| | | |
|---|---|---|
| EP | 0 524 404 A1 | 1/1993 |
| EP | 0 953 598 A1 | 11/1999 |
| EP | 2 350 187 A1 | 8/2011 |
| WO | WO 2000/069967 A1 | 11/2000 |
| WO | WO 02/20528 A2 | 3/2002 |
| WO | WO 2016/109708 A1 | 7/2016 |

OTHER PUBLICATIONS

PCT/US2016/067312 International Search Report, filed Dec. 16, 2016, 5 pages.
PCT/US2016/067312 Written Opinion of the International Searching Authority, filed Dec. 16, 2016, 5 pages.

* cited by examiner

*Primary Examiner* — Hui H Chin
(74) *Attorney, Agent, or Firm* — Robert M. Lanning

(57) ABSTRACT

An additive composition comprises 1,3:2,4-bis-O-[(3,4-dichlorophenyl)methylene]-D-glucitol and a low amount of residual acid. A polyolefin composition comprises a polyolefin polymer and the additive composition described above.

17 Claims, No Drawings

CLARIFYING AGENT COMPOSITION AND POLYOLEFIN COMPOSITION COMPRISING THE SAME

CROSS REFERENCE TO RELATED APPLICATIONS

This application claims, pursuant to 35 U.S.C. § 119(e)(1), priority to and the benefit of the filing date of U.S. Patent Application No. 62/274,096 filed on Dec. 31, 2016, which application is hereby incorporated by reference in its entirety.

TECHNICAL FIELD OF THE INVENTION

This application relates to clarifying agent compositions and polyolefin compositions comprising the same.

BRIEF SUMMARY OF THE INVENTION

The invention generally provides clarifying agent compositions that exhibit increased thermal stability and are capable of improving the haze levels of polyolefin polymers. The invention also provides polyolefin compositions comprising such clarifying agent compositions.

In a first embodiment, the invention provides an additive composition comprising 1,3:2,4-bis-O-[(3,4-dichlorophenyl)methylene]-D-glucitol, wherein the additive composition comprises less than 0.052 mol. % of acid based on the amount of 1,3:2,4-bis-O-[(3,4-dichlorophenyl)methylene]-D-glucitol present in the additive composition.

In a second embodiment, the invention provides a polyolefin composition comprising:
(a) a polyolefin polymer; and
(b) an additive composition, the additive composition comprising 1,3:2,4-bis-O-[(3,4-dichlorophenyl)methylene]-D-glucitol, wherein the additive composition comprises less than 0.052 mol. % of acid based on the amount of 1,3:2,4-bis-O-[(3,4-dichlorophenyl)methylene]-D-glucitol present in the composition.

DETAILED DESCRIPTION OF THE INVENTION

In a first embodiment, the invention provides an additive composition comprising 1,3:2,4-bis-O-[(3,4-dichlorophenyl)methylene]-D-glucitol and a relatively low amount of acid. The acid is a catalyst used in the production of the acetal compound. In particular, the acid is used to catalyze the condensation reaction between the alditol (i.e., D-glucitol) and the aldehyde compound (i.e., 3,4-dichlorobenzenecarbaldehyde).

The acid can be any suitable acid that catalyzes the reaction between the alditol and the aldehyde. Suitable acids include Lewis acids and Brønsted acids. The acid can be an inorganic acid (e.g., a mineral acid) or an organic acid. Preferably, the acid is selected from the group consisting of p-toluenesulfonic acid, methanesulfonic acid, sulfuric acid, phosphoric acid, hydrochloric acid, hypophosphorous acid, trifluoroacetic acid, triflic acid, and mixtures thereof. More preferably, the acid is p-toluenesulfonic acid.

The acid preferably is present in the additive composition in an amount of less than 0.052 mol. % based on the amount of 1,3:2,4-bis-O-[(3,4-dichlorophenyl)methylene]-D-glucitol present in the additive composition. More preferably, the acid is present in the additive composition in an amount of about 0.05 mol. % or less based on the amount of 1,3:2,4-bis-O-[(3,4-dichlorophenyl)methylene]-D-glucitol present in the additive composition. In another preferred embodiment, the acid is present in the additive composition in an amount of about 0.0475 mol. % or less based on the amount of 1,3:2,4-bis-O-[(3,4-dichlorophenyl)methylene]-D-glucitol present in the additive composition. In yet another preferred embodiment, the acid is present in the additive composition in an amount of about 0.045 mol. % or less based on the amount of 1,3:2,4-bis-O-[(3,4-dichlorophenyl)methylene]-D-glucitol present in the additive composition. In another preferred embodiment, the acid is present in the additive composition in an amount of about 0.036 mol. % or less based on the amount of 1,3:2,4-bis-O-[(3,4-dichlorophenyl)methylene]-D-glucitol present in the additive composition. In yet another preferred embodiment, the acid is present in the additive composition in an amount of about 0.03 mol. % or less based on the amount of 1,3:2,4-bis-O-[(3,4-dichlorophenyl)methylene]-D-glucitol present in the additive composition. In another preferred embodiment, the acid is present in the additive composition in an amount of about 0.022 mol. % or less based on the amount of 1,3:2,4-bis-O-[(3,4-dichlorophenyl)methylene]-D-glucitol present in the additive composition. In yet another preferred embodiment, the acid is present in the additive composition in an amount of about 0.015 mol. % or less based on the amount of 1,3:2,4-bis-O-[(3,4-dichlorophenyl)methylene]-D-glucitol present in the additive composition.

As noted above, the composition comprises 1,3:2,4-bis-O-[(3,4-dichlorophenyl)methylene]-D-glucitol. This compound is an acetal that can be produced by the reaction of an alditol with a substituted benzenecarbaldehyde compound. More specifically, the compound can be produced by the reaction of approximately 1 mole of D-glucitol with approximately 2 moles of 3,4-dichlorobenzenecarbaldehyde. The 1,3:2,4-bis-O-[(3,4-dichlorophenyl)methylene]-D-glucitol can be provided in any suitable physical form, but generally the compound is provided in the form of a powder.

As noted above, the 1,3:2,4-bis-O-[(3,4-dichlorophenyl)methylene]-D-glucitol typically is provided in the form of a powder, which powder contains many fine particles. The particles present in the powder generally are grouped into three different particle types of increasing size and complexity: primary particles; aggregates; and agglomerates. The primary particles generally are single crystals of the compound or fragments of such single crystals. The aggregates are comprised of two or more primary particles that have become strongly bound to each other. The aggregates cannot be reduced in size (e.g., reduced to their constituent primary particles) except through milling. The agglomerates are comprised of several primary particles and/or aggregates that have become weakly associated or bound together. The agglomerates can be reduced in size (e.g., broken apart and reduced to their constituent primary particles and/or aggregates) by the application of relatively modest mechanical forces. For example, the agglomerates can be reduced in size upon dispersion in a suitable liquid medium. The agglomerates typically contain relatively large voids within their interior dimensions, and these voids are filled with air. When such agglomerates are dispersed in the molten polymer during processing, the agglomerates break apart as the compound dissolves in the molten polymer. The air trapped in the voids can then become entrained in the molten polymer, and this entrained air leads to the formation of defects (e.g., white specks and/or bubbles) in the polymer composition.

The powder can have any suitable particle size. However, in order to facilitate dissolution of the compounds in the molten polymer and prevent the formation of defects (e.g., white specks or bubbles) in the polymer composition, it is advantageous for the particles to have a relatively small particle size. In a preferred embodiment, the volume mean diameter (i.e., the D[4,3]) of the 1,3:2,4-bis-O-[(3,4-dichlorophenyl)methylene]-D-glucitol particles is about 40 µm or less, about 35 µm or less, about 30 µm or less, or about 25 µm or less. Further, the $D_{90}$ of the 1,3:2,4-bis-O-[(3,4-dichlorophenyl)methylene]-D-glucitol particles preferably is about 80 µm or less, about 75 µm or less, about 70 µm or less, about 65 µm or less, about 60 µm or less, or about 55 µm or less.

The particle size of the 1,3:2,4-bis-O-[(3,4-dichlorophenyl)methylene]-D-glucitol can be measured using any suitable technique. For example, the particle size of the powder can be measured via dynamic light scattering using one of the many commercially available instruments designed for such measurements. When a dynamic light scattering technique is used, a representative sample of the particles generally is dispersed in a liquid medium and a sample of this liquid medium is introduced into the dynamic light scattering instrument. Any suitable liquid medium can be used, but water generally is the preferred medium. In order to facilitate dispersion of the particles in the liquid medium, a surfactant, preferably a non-ionic surfactant (e.g., an octylphenol surfactant), can be added to the water and the resulting mixture (i.e., water, surfactant, and particles) can be stirred for a sufficient time for the particles to disperse (e.g., for 1-5 minutes).

In certain possibly preferred embodiments, the composition can comprise another acetal compound in addition to the 1,3:2,4-bis-O-[(3,4-dichlorophenyl)methylene]-D-glucitol. In a particularly preferred embodiment, the composition additionally comprises 1,3:2,4-bis-O-[(3,4-dimethylphenyl)methylene]-D-glucitol. The 1,3:2,4-bis-O-[(3,4-dimethylphenyl)methylene]-D-glucitol can be produced by the reaction of approximately 1 mole of D-glucitol with approximately 2 moles of o-xylenecarbaldehyde. The 1,3:2,4-bis-O-[(3,4-dimethylphenyl)methylene]-D-glucitol can be provided in any suitable physical form, but, as with the 1,3:2,4-bis-O-[(3,4-dichlorophenyl)methylene]-D-glucitol, the compound generally is provided in the form of a powder containing may fine particles.

The particle size of the 1,3:2,4-bis-O-[(3,4-dimethylphenyl)methylene]-D-glucitol can be the same (e.g., in terms of volume mean diameter, $D_{90}$, or both) as the particle size of the 1,3:2,4-bis-O-[(3,4-dichlorophenyl)methylene]-D-glucitol described above. Alternatively, the particle size of the 1,3:2,4-bis-O-[(3,4-dimethylphenyl)methylene]-D-glucitol can be smaller (e.g., in terms of volume mean diameter, $D_{90}$, or both) than the particle size of the 1,3:2,4-bis-O-[(3,4-dichlorophenyl)methylene]-D-glucitol. In a preferred embodiment, the volume mean diameter (i.e., the D[4,3]) of the 1,3:2,4-bis-O-[(3,4-dimethylphenyl)methylene]-D-glucitol particles is about 40 µm or less, about 35 µm or less, about 30 µm or less, about 25 µm or less, about 20 µm or less, about 15 µm or less, about 10 µm or less, or about 7.5 µm or less. Further, the $D_{90}$ of the 1,3:2,4-bis-O-[(3,4-dimethylphenyl)methylene]-D-glucitol particles preferably is about 80 µm or less, about 75 µm or less, about 70 µm or less, about 65 µm or less, about 60 µm or less, about 55 µm or less, about 50 µm or less, about 45 µm or less, about 40 µm or less, about 35 µm or less, about 30 µm or less, about 25 µm or less, about 20 µm or less, about 15 µm or less, about 10 µm or less, or about 7.5 µm or less.

When the composition comprises both 1,3:2,4-bis-O-[(3,4-dichlorophenyl)methylene]-D-glucitol and 1,3:2,4-bis-O-[(3,4-dimethylphenyl)methylene]-D-glucitol, the two compounds can be present in the polyolefin composition in any suitable relative amounts. For example, the ratio of the mass of 1,3:2,4-bis-O-[(3,4-dimethylphenyl)methylene]-D-glucitol present in the composition to the mass of 1,3:2,4-bis-O-[(3,4-dichlorophenyl)methylene]-D-glucitol present in the composition preferably can be about 9:1 or less, about 8:1 or less, about 7:1 or less, about 6:1 or less, about 5:1 or less, about 4:1 or less, or about 3:1 or less. The ratio of the mass of 1,3:2,4-bis-O-[(3,4-dimethylphenyl)methylene]-D-glucitol present in the composition to the mass of 1,3:2,4-bis-O-[(3,4-dichlorophenyl)methylene]-D-glucitol present in the composition preferably can be about 1:9 or more, about 1:8 or more, about 1:7 or more, about 1:6 or more, about 1:5 or more, about 1:4 or more, or about 1:3 or more. In one preferred embodiment, the ratio of the mass of 1,3:2,4-bis-O-[(3,4-dimethylphenyl)methylene]-D-glucitol present in the composition to the mass of 1,3:2,4-bis-O-[(3,4-dichlorophenyl)methylene]-D-glucitol present in the composition is about 9:1 to about 1:9. In a series of sequentially more preferred embodiments, the ratio of the mass of 1,3:2,4-bis-O-[(3,4-dimethylphenyl)methylene]-D-glucitol present in the composition to the mass of 1,3:2,4-bis-O-[(3,4-dichlorophenyl)methylene]-D-glucitol present in the composition is about 8:1 to about 1:8, about 7:1 to about 1:7, about 6:1 to about 1:6, about 5:1 to about 1:5, about 4:1 to about 1:4, or about 3:1 to about 1:3.

While not wishing to be bound to any particular theory, it is believed that relatively high amounts of residual acid in the additive composition can be detrimental to the performance of the additive composition as a clarifying agent for thermoplastic polymers. More specifically, it is believed that the presence of residual acid leads to the degradation of a portion of the acetal compound(s) present in the additive composition. This degradation of the acetal compound(s) can generate colored by-products, and these colored by-products can negatively affect the visual aesthetics of a polymer clarified with the additive. Also, the degradation of a portion of the acetal compounds in the additive composition will reduce the efficacy of the additive composition, since there will be a lower amount of acetal compounds available to clarify the polymer.

In a second embodiment, the invention provides a polyolefin composition comprising a polyolefin polymer and the additive composition of the first embodiment of the invention (i.e., the composition comprising 1,3:2,4-bis-O-[(3,4-dichlorophenyl)methylene]-D-glucitol and a low amount of residual acid).

The polyolefin composition comprises a polyolefin polymer. The polyolefin polymer can be any suitable polyolefin, such as a polypropylene, a polyethylene, a polybutylene, a poly(4-methyl-1-pentene), and a poly(vinyl cyclohexane). In a preferred embodiment, the thermoplastic polymer is a polyolefin selected from the group consisting of polypropylene homopolymers (e.g., atactic polypropylene homopolymer, isotactic polypropylene homopolymer, and syndiotactic polypropylene homopolymer), polypropylene copolymers (e.g., polypropylene random copolymers), polypropylene impact copolymers, and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylene-diene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %. The polyolefin polymers described above can be branched or cross-linked, such as the branching or cross-linking that results from the addition of additives that increase the melt strength of the polymer.

The polyolefin polymer (e.g., polypropylene polymer) used in the composition can be a polymer that has been manufactured to possess the apparent melt viscosity, Melt Flow Rate, and/or Flow Rate Ratio described below for the polyolefin composition. For example, polypropylene polymers suitable for use in the composition include those manufactured in such a manner that the polymer sold by the manufacturer possesses one of the apparent melt viscosity values recited below for the polyolefin composition. Alternatively, a virgin polypropylene polymer that does not possess the desired characteristics can be modified through the addition of one or more additives. For example, the polymer can be combined with an organic peroxide or a vis-breaking agent and melt processed (e.g., extruded) in order to modify one or more characteristics of the polymer. Examples of organic peroxides suitable for such use include but are not limited to: 2,5-dimethyl-2,5-di(tert-butylperoxy) hexane, 2,5-dimethyl-2,5-di(tert-butyl peroxy)hexyne-3,3,6, 6,9,9-pentamethyl-3-(ethyl acetate)-1,2,4,5-tetraoxy cyclononane, tert-butyl hydroperoxide, hydrogen peroxide, dicumyl peroxide, tert-butyl peroxy isopropyl carbonate, di-tert-butyl peroxide, p-chlorobenzoyl peroxide, dibenzoyl diperoxide, tert-butyl cumyl peroxide, tert-butyl hydroxyethyl peroxide, di-tert-amyl peroxide, 2,5-dimethylhexene-2,5-diperisononanoate, acetylcyclohexanesulphonyl peroxide, diisopropyl peroxydicarbonate, tert-amyl perneodecanoate, tert-butyl-perneodecanoate, tert-butylperpivalate, tert-amylperpivalate, bis(2,4-dichlorobenzoyl)peroxide, diisononanoyl peroxide, didecanoyl peroxide, dioctanoyl peroxide, dilauroyl peroxide, bis(2-methylbenzoyl) peroxide, disuccinoyl peroxide, diacetyl peroxide, dibenzoyl peroxide, tert-butyl per-2-ethylhexanoate, bis(4-chlorobenzoyl)peroxide, tert-butyl perisobutyrate, tert-butyl permaleate, 1,1-bis(tert-butylperoxy)-3,5,5-trimethylcyclohexane, 1,1-bis(tert-butylperoxy)cyclohexane, tert-butyl peroxyisopropyl carbonate, tert-butyl perisononaoate, 2,5-dimethylhexane 2,5-dibenzoate, tert-butyl peracetate, tert-amyl perbenzoate, tert-butyl perbenzoate, 2,2-bis(tert-butylperoxy)butane, 2,2-bis(tert-butylperoxy)propane, dicumyl peroxide, 2,5-dimethylhexane 2,5-di-tert-butylperoxid, 3-tert-butylperoxy-3-phenyl phthalide, di-tert-amyl peroxide, α,α'-bis(tert-butylperoxyisopropyl)benzene, 3,5-bis(tert-butylperoxy)-3,5-dimethyl-1,2-dioxolane, di-tert-butyl peroxide, 2,5-dimethylhexyne 2,5-di-tert-butyl peroxide, 3,3,6,6,9,9-hexamethyl-1,2,4,5-tetraoxacyclononane, p-menthane hydroperoxide, pinane hydroperoxide, diisopropylbenzene mono-α-hydroperoxide, cumene hydroperoxide or tert-butyl hydroperoxide.

When used as an additive to modify the characteristics of the polymer via melt processing of the polymer, the organic peroxide or vis-breaking agent can be present in the polymer composition (prior to melt processing) in any suitable amount. The suitable amount of organic peroxide will depend upon several factors, such as the particular polymer that is used in the composition, the starting properties of the polymer, and the desired change in the properties of the polymer. In a preferred embodiment, the organic peroxide can be present in the polymer composition (prior to melt processing) in an amount of about 10 ppm or more, about 50 ppm or more, or about 100 ppm or more, based on the total weight of the polymer composition. In another preferred embodiment, the organic peroxide can be present in the polymer composition (prior to melt processing) in an amount of about 1 wt. % (10,000 ppm) or less, about 0.5 wt. % (5,000 ppm) or less, about 0.4 wt. % (4,000 ppm) or less, about 0.3 wt. % (3,000 ppm) or less, about 0.2 wt. % (2,000 ppm) or less, or about 0.1 wt. % (1,000 ppm) or less, about 0.05 wt. % (about 500 ppm) or less based on the total weight of the polymer composition. Thus, in a series of preferred embodiments, the organic peroxide can be present in the polymer composition (prior to melt processing) in an amount of about 10 to about 5,000 ppm, about 50 to about 3,000 ppm, about 50 to about 2,000 ppm, or about 100 to about 1,000 ppm, based on the total weight of the polymer composition. As will be understood by those skilled in the art, the organic peroxide degrades and is consumed during the melt processing of the polymer composition. Therefore, the amount of organic peroxide present in the polymer composition after melt processing likely will not fall within the ranges recited above, and typically, the organic peroxide is not detectable in the polymer composition after melt processing.

The 1,3:2,4-bis-O-[(3,4-dichlorophenyl)methylene]-D-glucitol can be present in the polyolefin composition in any suitable absolute amount. Typically, the amount of 1,3:2,4-bis-O-[(3,4-dichlorophenyl)methylene]-D-glucitol present in the polyolefin composition is about 250 parts-per-million (ppm) or more based on the weight of the polymer (e.g., polypropylene polymer) present in the polyolefin composition. Preferably, the amount of 1,3:2,4-bis-O-[(3,4-dichlorophenyl)methylene]-D-glucitol present in the polyolefin composition is about 500 ppm or more, about 750 ppm or more, about 1,000 ppm or more, about 1,250 ppm or more, or about 1,500 ppm or more based on the weight of the polymer (e.g., polypropylene polymer) present in the polyolefin composition. The amount of 1,3:2,4-bis-O-[(3,4-dichlorophenyl)methylene]-D-glucitol present in the polyolefin composition typically is also about 4,000 ppm or less based on the weight of the polymer (e.g., polypropylene polymer) present in the polyolefin composition. Preferably, the amount of 1,3:2,4-bis-O-[(3,4-dichlorophenyl)methylene]-D-glucitol present in the polyolefin composition is about 3,500 ppm or less, about 3,000 ppm or less, about 2,750 ppm or less, about 2,500 ppm or less, about 2,250 ppm or less, or about 2,000 ppm or less based on the weight of the polymer (e.g., polypropylene polymer) present in the polyolefin composition. Thus, in a series of sequentially more preferred embodiments, the amount of 1,3:2,4-bis-O-[(3,4-dichlorophenyl)methylene]-D-glucitol present in the polyolefin composition is about 250 ppm to about 4,000 ppm, about 250 ppm to about 3,000 ppm, about 250 ppm to about 2,500 ppm, or about 500 ppm to about 2,000 ppm based on the weight of the polymer (e.g., polypropylene polymer) present in the polyolefin composition.

In certain possibly preferred embodiments, the polyolefin composition can comprise another acetal compound in addition to the 1,3:2,4-bis-O-[(3,4-dichlorophenyl)methylene]-D-glucitol. In a particularly preferred embodiment, the polyolefin composition additionally comprises 1,3:2,4-bis-O-[(3,4-dimethylphenyl)methylene]-D-glucitol. The 1,3:2,4-bis-O-[(3,4-dimethylphenyl)methylene]-D-glucitol can be produced by the reaction of approximately 1 mole of D-glucitol with approximately 2 moles of o-xylenecarbaldehyde. The 1,3:2,4-bis-O-[(3,4-dimethylphenyl)methylene]-D-glucitol can be provided in any suitable physical form, but, as with the 1,3:2,4-bis-O-[(3,4-dichlorophenyl)methylene]-D-glucitol, the compound generally is provided in the form of a powder containing many fine particles.

The particle size of the 1,3:2,4-bis-O-[(3,4-dimethylphenyl)methylene]-D-glucitol can be the same (e.g., in terms of volume mean diameter, $D_{90}$, or both) as the particle size of the 1,3:2,4-bis-O-[(3,4-dichlorophenyl)methylene]-D-glucitol described above. Alternatively, the particle size of the 1,3:2,4-bis-O-[(3,4-dimethylphenyl)methylene]-D-glucitol can be smaller (e.g., in terms of volume mean diameter, $D_{90}$, or both) than the particle size of the 1,3:2,4-bis-O-[(3,4-dichlorophenyl)methylene]-D-glucitol. In a preferred embodiment, the volume mean diameter (i.e., the D[4,3]) of the 1,3:2,4-bis-O-[(3,4-dimethylphenyl)methylene]-D-glucitol particles is about 40 µm or less, about 35 µm or less, about 30 µm or less, about 25 µm or less, about 20 µm or less, about 15 µm or less, about 10 µm or less, or about 7.5 µm or less. Further, the $D_{90}$ of the 1,3:2,4-bis-O-[(3,4-dimethylphenyl)methylene]-D-glucitol particles preferably is about 80 µm or less, about 75 µm or less, about 70 µm or less, about 65 µm or less, about 60 µm or less, about 55 µm or less, about 50 µm or less, about 45 µm or less, about 40 µm or less, about 35 µm or less, about 30 µm or less, about 25 µm or less, about 20 µm or less, about 15 µm or less, about 10 µm or less, or about 7.5 µm or less.

When present in the polyolefin composition, the 1,3:2,4-bis-O-[(3,4-dimethylphenyl)methylene]-D-glucitol can be present in any suitable amount. For example, the 1,3:2,4-bis-O-[(3,4-dimethylphenyl)methylene]-D-glucitol can be present in any of the amounts listed above for the 1,3:2,4-bis-O-[(3,4-dichlorophenyl)methylene]-D-glucitol. Alternatively, the combined amount of 1,3:2,4-bis-O-[(3,4-dichlorophenyl)methylene]-D-glucitol and 1,3:2,4-bis-O-[(3,4-dimethylphenyl)methylene]-D-glucitol present in the composition can fall within any of the ranges described above for the 1,3:2,4-bis-O-[(3,4-dichlorophenyl)methylene]-D-glucitol.

The polyolefin composition described herein can have any suitable apparent melt viscosity. The apparent melt viscosity of the polyolefin composition can be measured using any suitable method. For example, the apparent melt viscosity can be determining using the test method described in ASTM Test Method D3835-08 entitled "Standard Test Method for Determination of Properties of Polymeric Materials by Means of a Capillary Rheometer." While this test method provides that 220° C. is the testing temperature typically employed in testing polypropylene compositions, it is believed that 190° C. is a more suitable temperature since it better approximates the lower processing temperatures that are today employed with many commercial polymers. Thus, the apparent melt viscosities for the polypropylene-containing polyolefin compositions listed herein preferably are determined using the above-referenced test method at a temperature of 190° C. The apparent melt viscosity of the polyolefin composition can be measured at any suitable apparent shear rate. It is believed that an apparent shear rate of 100 $s^{-1}$ is preferred because it closely approximates the shear that a polymer composition experiences during typical processing conditions. When measuring the apparent melt viscosity of the polyolefin composition, the capillary rheometer preferably is equipped with a 1.00 mm diameter capillary die with a length to diameter ratio of 30:1. Further, the polyolefin composition preferably is allowed to remain in the capillary rheometer for a dwell time of six (6) minutes prior to beginning the test. Lastly, the apparent melt viscosity of the polyolefin composition preferably is determined after the polymer, the additive composition comprising the 1,3:2,4-bis-O-[(3,4-dichlorophenyl)methylene]-D-glucitol, and any optional components have been melt processed (e.g., passed through an extruder).

Preferably, the polyolefin composition has an apparent melt viscosity of about 750 Pa·s or less at an apparent shear rate of 100 $s^{-1}$. More preferably, the polyolefin composition has an apparent melt viscosity of about 700 Pa·s or less, about 650 Pa·s or less, about 600 Pa·s or less, about 550 Pa·s or less, about 500 Pa·s or less, about 450 Pa·s or less, about 400 Pa·s or less, about 350 Pa·s or less, about 300 Pa·s or less, about 250 Pa·s or less, or about 200 Pa·s or less at an apparent shear rate of 100 $s^{-1}$ and a temperature of 190° C.

The polyolefin composition described herein can have any suitable Melt Flow Rate. The Melt Flow Rate of the polyolefin composition can be determined by any suitable method. For example, the Melt Flow Rate of the polyolefin composition can be determined using Procedure B in ASTM Standard D1238-10 entitled "Standard Test Method for Melt Flow Rates of Thermoplastics by Extrusion Plastometer." The Melt Flow Rate of the polyolefin composition preferably is measured using the aforementioned standard test method. Preferably, the polyolefin composition has a Melt Flow Rate of 4 g/10 min or more. More preferably, the polyolefin composition has a Melt Flow Rate of about 8 g/10 min or more, about 10 g/10 min or more, about 12 g/10 min or more, about 20 g/10 min or more, about 35 g/10 min or more, or about 50 g/10 min or more. As in the measurement of the apparent melt viscosity, the Melt Flow Rate of the polyolefin composition preferably is determined after the polymer, the additive composition comprising the 1,3:2,4-bis-O-[(3,4-dichlorophenyl)methylene]-D-glucitol, and any optional components (e.g., peroxide) have been melt processed (e.g., passed through an extruder).

As will be understood by those of ordinary skill in the art, the polyolefin polymer will contain a population of discrete polymer chains, and those polymer chains will have varying lengths and molar masses. The statistical distribution of the lengths/molar masses of the polymer chains contained in the polymer is generally referred to as the molar mass distribution or molecular weight distribution. The polyolefin polymers used in the compositions described herein can have any suitable molar mass distribution. For example, the polyolefin polymer can have a molar mass distribution exhibiting a single mode or the molar mass distribution can exhibit a plurality of modes (e.g., bimodal, trimodal, etc.). The breadth of the molar mass distribution of a polymer can be expressed using the polydispersity index. The polydispersity index is calculated by measuring the number average molar mass and the mass average molar mass (i.e., weight average molar mass) of the polymer, and then dividing the mass average molar mass of the polymer by the number average molar mass of the polymer. The result is a dimensionless unit that quantifies the breadth of the molar mass distribution, with higher values indicating greater breadth in the molar mass distribution. The breadth of the molar mass distribution can also be indirectly quantified by measuring and comparing the Melt Flow Rate of the polymer (or a composition containing the polymer) under different conditions to yield a Flow Rate Ratio (FRR). This method is described, for example, in Procedure D of ASTM Standard D1238 entitled "Standard Test Method for Melt Flow Rates of Thermoplastics by Extrusion Plastometer." Preferably, the FRR is calculated using the Melt Flow Rate measured using the 10 kg weight specified in the standard ($MFR_{10}$) and the Melt Flow Rate measured using the 2 kg weight specified in the standard ($MFR_2$). The polyolefin composition described herein can have any suitable FRR. Preferably, the polyolefin composition has a FRR ($MFR_{10}/MFR_2$) of about 17 or less. More preferably, the polyolefin composition has a FRR ($MFR_{10}/MFR_2$) of about 16 or less or about 15 or less. As in measuring the apparent melt viscosity and the Melt Flow Rate, the Flow Rate Ratio of the polyolefin composition preferably is determined after the polymer, the additive composition comprising the 1,3:2,4-bis-O-[(3,4-dichloro-phenyl)methylene]-D-glucitol, and any optional components (e.g., peroxide) have been melt processed (e.g., passed through an extruder).

The polyolefin composition described herein can contain other polymer additives in addition to the 1,3:2,4-bis-O-[(3,4-dichlorophenyl)methylene]-D-glucitol. Suitable additional polymer additives include, but are not limited to, antioxidants (e.g., phenolic antioxidants, phosphite antioxidants, and combinations thereof), anti-blocking agents (e.g., amorphous silica and diatomaceous earth), pigments (e.g., organic pigments and inorganic pigments) and other colorants (e.g., dyes and polymeric colorants), fillers and reinforcing agents (e.g., glass, glass fibers, talc, calcium carbonate, and magnesium oxysulfate whiskers), nucleating agents, clarifying agents, acid scavengers (e.g., metal salts of fatty acids, such as the metal salts of stearic acid), polymer processing additives (e.g., fluoropolymer polymer processing additives), polymer cross-linking agents, slip agents (e.g., fatty acid amide compounds derived from the reaction between a fatty acid and ammonia or an amine-containing compound), fatty acid ester compounds (e.g., fatty acid ester compounds derived from the reaction between a fatty acid and a hydroxyl-containing compound, such as glycerol, diglycerol, and combinations thereof), and combinations of the foregoing.

As noted above, the polyolefin composition can contain nucleating agents in addition to the other components described above. Suitable nucleating agents include, but are not limited to, 2,2'-methylene-bis-(4,6-di-tert-butylphenyl) phosphate salts (e.g., sodium 2,2'-methylene-bis-(4,6-di-tert-butylphenyl) phosphate or aluminum 2,2'-methylene-bis-(4,6-di-tert-butylphenyl)phosphate), bicyclo[2.2.1]heptane-2,3-dicarboxylate salts (e.g., disodium bicyclo[2.2.1]heptane-2,3-dicarboxylate or calcium bicyclo[2.2.1]heptane-2,3-dicarboxylate), cyclohexane-1,2-dicarboxylate salts (e.g., calcium cyclohexane-1,2-dicarboxylate, monobasic aluminum cyclohexane-1,2-dicarboxylate, dilithium cyclohexane-1,2-dicarboxylate, or strontium cyclohexane-1,2-dicarboxylate), and combinations thereof. For the bicyclo[2.2.1]heptane-2,3-dicarboxylate salts and the cyclohexane-1,2-dicarboxylate salts, the carboxylate moieties can be arranged in either the cis- or trans-configuration, with the cis-configuration being preferred.

As noted above, the polyolefin composition can also contain one or more additional clarifying agents. Suitable clarifying agents include, but are not limited to, trisamides and acetal compounds that are the condensation product of a polyhydric alcohol and an aromatic aldehyde. Suitable trisamide clarifying agents include, but are not limited to, amide derivatives of benzene-1,3,5-tricarboxylic acid, amide derivatives of 1,3,5-benzenetriamine, derivatives of N-(3,5-bis-formylamino-phenyl)-formamide (e.g., N-[3,5-bis-(2,2-dimethyl-propionylamino)-phenyl]-2,2-dimethyl-propionamide), derivatives of 2-carbamoyl-malonamide (e.g., N,N'-bis-(2-methyl-cyclohexyl)-2-(2-methyl-cyclo-hexylcarbamoyl)-malonamide), and combinations thereof. As noted above, the clarifying agent can be an acetal compound that is the condensation product of a polyhydric alcohol and an aromatic aldehyde. Suitable polyhydric alcohols include acyclic polyols such as xylitol and sorbitol, as well as acyclic deoxy polyols (e.g., 1,2,3-trideoxynonitol or 1,2,3-trideoxynon-1-enitol). Suitable aromatic aldehydes typically contain a single aldehyde group with the remaining positions on the aromatic ring being either unsubstituted or substituted. Accordingly, suitable aromatic aldehydes include benzaldehyde and substituted benzaldehydes (e.g., 3,4-dimethyl-benzaldehyde or 4-propyl-benzaldehyde). The acetal compound produced by the aforementioned reaction can be a mono-acetal, di-acetal, or tri-acetal compound (i.e., a compound containing one, two, or three acetal groups, respectively), with the di-acetal compounds being preferred. Suitable acetal-based clarifying agents include, but are not limited to, the clarifying agents disclosed in U.S. Pat. Nos. 5,049,605; 7,157,510; and 7,262,236.

The polyolefin composition described herein can be produced by any suitable method. For example, the polyolefin composition can be produced by simple mixing (e.g., high shear or high intensity mixing) of the polyolefin polymer, the additive composition comprising the 1,3:2,4-bis-O-[(3,4-dichlorophenyl)methylene]-D-glucitol, and any additional optional components. Alternatively, the additive composition comprising the 1,3:2,4-bis-O-[(3,4-dichlorophenyl)methylene]-D-glucitol and any additional optional components (such as those described above) can be pre-blended to provide a pre-blend composition. This pre-blend composition can then be mixed with the polyolefin polymer to produce the polyolefin composition described above. The polyolefin composition can be provided in any form suitable for use in further processing to produce an article. For example, the polyolefin composition can be provided in the form of a powder (e.g., free-flowing powder), flake, pellet, prill, tablet, agglomerate, and the like.

The polyolefin composition described herein is believed to be useful in producing thermoplastic articles. The polyolefin compositions can be formed into the desired thermoplastic article by any suitable technique, such as injection molding, injection rotational molding, blow molding (e.g., injection blow molding or injection stretch blow molding), extrusion (e.g., sheet extrusion, film extrusion, cast film extrusion, or foam extrusion), extrusion blow molding, thermoforming, rotomolding, film blowing (blown film), film casting (cast film), and the like.

The polyolefin composition described herein can be used to produce any suitable article or product. Suitable products include, but are not limited to, medical devices (e.g., pre-filled syringes for retort applications, intravenous supply containers, and blood collection apparatus), food packaging, liquid containers (e.g., containers for drinks, medications, personal care compositions, shampoos, and the like), apparel cases, microwavable articles, shelving, cabinet doors, mechanical parts, automobile parts, sheets, pipes, tubes, rotationally molded parts, blow molded parts, films, fibers, and the like.

The following examples further illustrate the subject matter described above but, of course, should not be construed as in any way limiting the scope thereof.

EXAMPLE 1

This example demonstrates the performance of several different additive compositions comprising 1,3:2,4-bis-O-[(3,4-dichlorophenyl)methylene]-D-glucitol and varying levels of residual acid catalyst.

Nine samples of 1,3:2,4-bis-O-[(3,4-dichlorophenyl)methylene]-D-glucitol containing varying levels of residual acid (Samples 1-9) were prepared. The 1,3:2,4-bis-O-[(3,4-dichlorophenyl)methylene]-D-glucitol was synthesized by reacting in a condensation reaction D-glucitol and 3,4-dichloroebenzenecarbaldehyde in a 1:2 stoichiometric ratio. The reaction was catalyzed with p-toluenesulfonic acid. To obtain Samples 1-9, the product of the reaction was washed, dried, and otherwise treated to yield varying levels of residual acid. The level of residual acid present in each sample was quantified using High Pressure Liquid Chromatography and is reported in Table 1 below.

The color stability of each sample was also characterized using the following method. Approximately 30 mg of the sample was weighed in an aluminum weigh pan. Then, the pan was placed into an oven held at a temperature of approximately 240° C. for 5 minutes. After this thermal treatment, the visual appearance of the sample was noted and recorded. These results are also reported in Table 1 below.

TABLE 1

Acid Amounts and Thermal Stability of Samples 1-9.

| Sample | Mol. % Acid | Observations after thermal test |
| --- | --- | --- |
| 1 | 0.058 | Partially melted & brown color |
| 2 | 0.52 | Partially melted & brown color |
| 3 | 0.047 | Slight discoloration |
| 4 | 0.044 | Slight discoloration |
| 5 | 0.039 | Slight discoloration |
| 6 | 0.038 | Slight discoloration |
| 7 | 0.029 | Slight discoloration |
| 8 | 0.0052 | Slight discoloration |
| 9 | <0.0003 | No discoloration |

As can be seen from the data in Table 1, the concentration of residual acid in a sample affects the performance of the 1,3:2,4-bis-O-[(3,4-dichlorophenyl)methylene]-D-glucitol. When the acid content of the sample was 0.052 mol. % or greater, the sample degraded, liquefied, and discolored upon heating to a temperature approximating those used in polymer processing. At levels of acid lower than 0.052 mol. %, the sample remained a solid and was only slightly discolored when heated to the same temperature. This is believed to demonstrate that the samples containing lower residual acid will perform better as clarifying agents for the polymer.

The clarifying performance of Samples 1 and 8 was assessed using the following method. A one-kilogram batch of a polypropylene random copolymer composition was compounded with 0.40 g calcium stearate, 0.50 g Irganox® 1010, 1.0 g Irgafos® 168, and 1.5 g of the sample. The polypropylene random copolymer used in the compositions was Pro-fax SA849 polypropylene random copolymer from LyondellBasell Polymers, which had an initial Melt Flow Rate of approximately 12 g/10 min. The polypropylene composition was compounded by blending the components in a Henschel high intensity mixer for approximately 1 minute at a blade speed of approximately 2,100 rpm. The resulting polymer composition was then melt compounded on a Deltaplast single screw compounding extruder with a 25 mm screw diameter and length/diameter ratio of 30:1. The barrel temperature was ramped from about 200° C. to about 230° C. using six heating zones. The extrudate (in the form a strand) for each sample was cooled in a water bath and subsequently pelletized. Pellets of each polymer composition were then molded into plaques with dimensions of approximately 51 mm×76 mm with a thickness of 1.27 mm using an Arburg 25 ton injection molder. All molder barrel zones were set to 230° C., and the mold was cooled to 21° C. Plaque dimensions were verified with a micrometer after aging for 24 hours. The haze of the resulting plaques was measured in accordance with ASTM Standard D1103-92 using a BYK-Gardner Haze-Guard Plus. The measured percent haze for the polymer composition containing Sample 1 was 24%. The measured percent haze for the polymer composition containing Sample 8 was 20%. This data demonstrates how lower levels of residual acid improve the performance of the clarifying agent.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. An additive composition comprising 1,3:2,4-bis-O-[(3,4-dichlorophenyl)methylene]-D-glucitol, wherein the additive composition comprises greater than 0 mol. % and less than 0.052 mol. % of Brønsted acid based on the amount of 1,3:2,4-bis-O-[(3,4-dichlorophenyl)methylene]-D-glucitol present in the additive composition.

2. The additive composition of claim 1, wherein the additive composition comprises about 0.05 mol. % or less of Brønsted acid based on the amount of 1,3:2,4-bis-O-[(3,4-dichlorophenyl)methylene]-D-glucitol present in the additive composition.

3. The additive composition of claim 1, wherein the additive composition comprises about 0.0475 mol. % or less of Brønsted acid based on the amount of 1,3:2,4-bis-O-[(3,4-dichlorophenyl)methylene]-D-glucitol present in the additive composition.

4. The additive composition of claim 1, wherein the additive composition comprises about 0.045 mol. % or less of Brønsted acid based on the amount of 1,3:2,4-bis-O-[(3,4-dichlorophenyl)methylene]-D-glucitol present in the additive composition.

5. The additive composition of claim 1, wherein the Brønsted acid is selected from the group consisting of p-toluenesulfonic acid, methanesulfonic acid, sulfuric acid, phosphoric acid, hydrochloric acid, hypophosphorous acid, trifluoroacetic acid, triflic acid, and mixtures thereof.

6. The additive composition of claim 1, wherein the composition further comprises 1,3:2,4-bis-O-[(3,4-dimethylphenyl)methylene]-D-glucitol.

7. The additive composition of claim 6, wherein the ratio of the mass of 1,3:2,4-bis-O-[(3,4-dimethylphenyl)methylene]-D-glucitol present in the additive composition to the mass of 1,3:2,4-bis-O-[(3,4-dichlorophenyl)methylene]-D-glucitol present in the additive composition is about 9:1 to about 1:9.

8. A polyolefin composition comprising:
(a) a polyolefin polymer; and
(b) an additive composition, the additive composition comprising 1,3:2,4-bis-O-[(3,4-dichlorophenyl)methylene]-D-glucitol, wherein the additive composition comprises greater than 0 mol. % and less than 0.052 mol. % of Brønsted acid based on the amount of 1,3:2,4-bis-O-[(3,4-dichlorophenyl)methylene]-D-glucitol present in the additive composition.

9. The polyolefin composition of claim 8, wherein the additive composition comprises about 0.05 mol. % or less of Brønsted acid based on the amount of 1,3:2,4-bis-O-[(3,4-dichlorophenyl)methylene]-D-glucitol present in the additive composition.

10. The polyolefin composition of claim 8, wherein the additive composition comprises about 0.0475 mol. % or less of Brønsted acid based on the amount of 1,3:2,4-bis-O-[(3,4-dichlorophenyl)methylene]-D-glucitol present in the additive composition.

11. The polyolefin composition of claim 8, wherein the additive composition comprises about 0.045 mol. % or less of Brønsted acid based on the amount of 1,3:2,4-bis-O-[(3,4-dichlorophenyl)methylene]-D-glucitol present in the additive composition.

12. The polyolefin composition of claim 8, wherein the 1,3:2,4-bis-O-[(3,4-dichlorophenyl)methylene]-D-glucitol is present in the polyolefin composition in an amount of about 250 ppm to about 3,000 ppm based on the total weight of the polyolefin composition.

13. The polyolefin composition of claim 12, wherein the 1,3:2,4-bis-O-[(3,4-dichlorophenyl)methylene]-D-glucitol is present in the polyolefin composition in an amount of about 500 ppm to about 2,000 ppm based on the total weight of the polyolefin composition.

14. The polyolefin composition of claim 8, wherein the polyolefin composition further comprises 1,3:2,4-bis-O-[(3,4-dimethylphenyl)methylene]-D-glucitol.

15. The polyolefin composition of claim 14, wherein the ratio of the mass of 1,3:2,4-bis-O-[(3,4-dimethylphenyl)methylene]-D-glucitol present in the polyolefin composition to the mass of 1,3:2,4-bis-O-[(3,4-dichlorophenyl)methylene]-D-glucitol present in the polyolefin composition is about 9:1 to about 1:9.

16. The polyolefin composition of claim 14, wherein the total amount of 1,3:2,4-bis-O[(3,4-dichlorophenyl)methylene]-D-glucitol and 1,3:2,4-bis-O-[(3,4-dichlorophenyl)methylene]-D-glucitol present in the polyolefin composition is about 250 ppm to about 3,000 ppm based on the total weight of the polyolefin composition.

17. The polyolefin composition of claim 16, wherein the total amount of 1,3:2,4-bis-O-[(3,4-dichlorophenyl)methylene]-D-glucitol and 1,3:2,4-bis-O-[(3,4-dichlorophenyl)methylene]-D-glucitol present in the polyolefin composition is about 500 ppm to about 2,000 ppm based on the total weight of the polyolefin composition.

* * * * *